(12) United States Patent
Beilfuss et al.

(10) Patent No.: US 6,956,062 B2
(45) Date of Patent: Oct. 18, 2005

(54) STORAGE-STABLE COMPOSITIONS OF GLYCEROL MONOALKYL ETHERS

(75) Inventors: Wolfgang Beilfuss, Hamburg (DE); Ralf Gradtke, Tornesh (DE)

(73) Assignee: Air Liquide Santé (International), Paris (FR)

( * ) Notice: Subject to any disclaimer, the term of this patent is extended or adjusted under 35 U.S.C. 154(b) by 34 days.

(21) Appl. No.: 10/297,795

(22) PCT Filed: May 17, 2001

(86) PCT No.: PCT/IB01/00865

§ 371 (c)(1),
(2), (4) Date: Dec. 9, 2002

(87) PCT Pub. No.: WO01/93825

PCT Pub. Date: Dec. 13, 2001

(65) Prior Publication Data

US 2003/0149097 A1 Aug. 7, 2003

(30) Foreign Application Priority Data

Jun. 9, 2000 (DE) .......................... 100 28 638

(51) Int. Cl.$^7$ ..................... A61K 31/08; A61K 30/355
(52) U.S. Cl. ........................ 514/723; 514/458
(58) Field of Search .................. 514/723, 458

(56) References Cited

U.S. PATENT DOCUMENTS

| | | | | |
|---|---|---|---|---|
| 5,446,033 A | * | 8/1995 | Engel et al. ................... 514/77 |
| 5,516,510 A | | 5/1996 | Beilfuss et al. |
| 5,621,012 A | * | 4/1997 | Sch onrock et al. ......... 514/629 |
| 5,736,574 A | * | 4/1998 | Burnier et al. ............... 514/563 |
| 6,040,347 A | * | 3/2000 | Cupferman et al. ......... 514/723 |
| 6,221,816 B1 | * | 4/2001 | Kasuga et al. ............... 510/119 |

FOREIGN PATENT DOCUMENTS

| | | |
|---|---|---|
| DE | 41 40 474 A1 | 12/1991 |
| DE | 44 20 625 C1 | 11/1995 |
| EP | 0 471 084 A1 | 3/1991 |
| EP | 0471084 A1 * | 9/1991 |
| EP | 0 593 897 B1 | 9/1993 |
| EP | 0 599 433 A1 | 11/1993 |
| EP | 0 769 291 A1 | 9/1996 |
| JP | 09-030919 * | 2/1997 |
| WO | WO 99/11 237 A1 | 8/1998 |
| WO | WO99/11237 * | 3/1999 |

OTHER PUBLICATIONS

Siegert et al, Sensiva SC 50 ® product information, Schulke & Mayr Gnbh, Germany.*

* cited by examiner

*Primary Examiner*—Vickie Kim
(74) *Attorney, Agent, or Firm*—Linda K. Russell

(57) ABSTRACT

The present invention relates to compositions which comprise a combination
a) of one or more glycerol monoalkyl ether(s) of the general formula

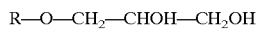

$$R-O-CH_2-CHOH-CH_2OH$$

in which R is a branched or unbranched $C_3$–$C_{18}$-alkyl group, where the alkyl group can be substituted by one or more hydroxyl and/or $C_1$–$C_4$-alkoxy group(s) and/or the alkyl chain can be interrupted by up to four oxygen atoms, with
b) an antioxidant or two or more antioxidants as stabilizer(s), the simultaneous presence of phosphocholines and phosphocholine derivatives being excluded.

12 Claims, No Drawings

STORAGE-STABLE COMPOSITIONS OF GLYCEROL MONOALKYL ETHERS

BACKGROUND

The present invention relates to compositions comprising glycerol monoalkyl ethers for use in cosmetic and pharmaceutical preparations and in technical products. These compositions have in particular good long-term storage stability and comprise at least one glycerol monoalkyl ether and at least one antioxidant as stabilizer.

Of the two substitution-isomeric glycerol monoalkyl ethers (2-alkoxy-1,3-propanediols and 3-alkoxy-1,2-propanediols), the present invention relates in particular to the 3-alkoxy-1,2-propanediols.

The invention further relates to concentrates and working solutions. The compositions according to the invention, i.e. in particular the concentrates and working solutions, are added to pharmaceutical and cosmetic preparations and technical products.

Glycerol monoalkyl ethers are used as additives for cosmetic and pharmaceutical preparations and have a multifaceted action. Thus, for example, they are used as physiologically compatible organic solvents. In particular, 3-[(2-ethylhexyl)oxy]-1,2-propanediol (Sensiva® SC 50) has been used increasingly for some years as a deodorant active ingredient and skin care additive in cosmetic and pharmaceutical preparations. Here, the glycerol monoalkyl ethers are added to the preparations or technical products usually in the form of a concentrate or as a pure glycerol monoalkyl ether.

During manufacture, storage and use, the glycerol monoalkyl ether, its concentrate and its dilute solution (working solution) are subject to high requirements which arise from the increased demands of the consumer on the quality of cosmetic and pharmaceutical preparations.

The glycerol monoalkyl ethers are largely chemically stable and stable to external atmospheric influences. They are often colourless, almost odourless liquids and, because of their good chemical stability, are highly compatible with most cosmetic and pharmaceutical ingredients. Because glycerol monoalkyl ethers occur naturally, even the synthetically prepared representatives of the class of substance are particularly desirable for use in end-products because they are widely accepted by manufacturers of cosmetics and pharmaceuticals and end users.

DE 41 40 474 A1 describes the use of certain glycerol monoalkyl ethers in particular as skin care additive for products from the cosmetic and pharmaceutical and quasi-cosmetic sector and emphasizes their high chemical stability.

EP 0 599 433 A1 discloses that glycerol monoalkyl ethers exhibit effectiveness against odour-causing Gram-positive bacteria. In this connection, deodorizing glycerol monoalkyl ethers of a specifically low-odour and low-peroxide quality are particularly preferred.

EP 0 593 897 A1 discloses aqueous phosphocholine preparations in which glycerol monoalkyl ethers, i.e. 3-alkoxy-1,2-propanediols and 2-alkoxy-1,3-propanediols, are used as physiologically compatible organic solvents. The pharmaceutical preparations disclosed therein are not storage-stable even in the presence of antioxidants. In EP 0 593 897 A1, the stability is improved by the addition of a buffer.

We have now found that the storage stability, in particular the long-term storage stability (over several months to years), with regard to the peroxide content of preparations comprising glycerol monoalkyl ethers is unsatisfactory. Thus, for example, manufacturers of cosmetics complain that incompatibilities between glycerol monoalkyl ethers and formulation constituents or changes in quality of the end-products have been established. The cause of these losses in quality may inter alia be a formation of peroxide which takes place in the preparations depending on the time and storage. The peroxide content in stored preparations varies comparatively greatly and cannot be calculated (chaotic development of the peroxide number, see Experiments A and A (Alu) in Table 1 in Example 1). Furthermore, the appearance of undesired degradation products of low molecular weight was detected by chemical analysis.

The disadvantages of traditional preparations comprising glycerol monoalkyl ethers arise in concentrated and dilute glycerol monoalkyl ether solutions or finished products and can be summarized as follows:
1. Peroxides in cosmetic and pharmaceutical preparations, in particular skin care compositions, when used on the skin of persons with a predisposition, trigger the clinical picture of Mallorca acne (a light dermatosis).
2. A change in the odour of stored precursors or products or stored glycerol monoalkyl ethers results.
3. A change in the odour of cosmetic products as a result of oxidation of natural fats and oils present therein results.
4. Greying of oil-in-water emulsions comprising glycerol monoalkyl ethers arises as a result of incompatibilities of stored mixtures with ingredients of cosmetics and pharmaceuticals.
5. Degradation products of low molecular weight can be detected by chemical analysis.
6. The abovementioned disadvantages can lead to toxicological expert opinions which have a tendency to be relatively unfavourable for cosmetics and pharmaceuticals which have been prepared using stored glycerol monoalkyl ethers.
7. The mixtures, e.g. glycerol monoalkyl ether concentrates, are usually stored in plastic containers. During storage, permanent deformations of plastic containers have been observed, which is referred to as the neck-in effect. Containers with a severe neck-in effect can no longer be stacked safely.
8. Regular quality control of stored glycerol monoalkyl ethers by the cosmetics and pharmaceuticals manufacturers is technologically laborious, long-term storage of glycerol monoalkyl ethers cannot always be avoided and the disposal of amounts of glycerol monoalkyl ethers which have become unusable causes additional costs.

SUMMARY

Accordingly, the object of the present invention is to provide compositions which comprise one or more glycerol monoalkyl ethers, the intention being for these compositions to be storage-stable, in particular storage-stable for a long period, and be storable and stable under practical conditions. Preferably, the abovementioned disadvantages should not arise during storage up to 60 months, more preferably 12 to 36 months, e.g. 12 months or 24 months. A further object of the present invention is to provide stabilizers which can be used for the long-term stabilization of glycerol monoalkyl ethers. These stabilizers should, added in a low mixing ratio to glycerol monoalkyl ethers or preparations comprising glycerol monoalkyl ethers, protect these preparations from decomposition, in particular with the development of high peroxide numbers.

DESCRIPTION OF PREFERRED EMBODIMENTS

These objects are achieved by the present invention. According to Patent Claim 1, the stable composition is characterized in that it comprises a combination a) of one or more glycerol monoalkyl ether(s) of the general formula

R—O—CH$_2$—CHOH—CH$_2$OH in which R is a branched or unbranched C$_3$–C$_{18}$-alkyl group, where the alkyl group can be substituted by one or more hydroxyl and/or C$_1$–C$_4$-alkoxy group(s) and/or the alkyl chain can be interrupted by up to four oxygen atoms, with b) an antioxidant or two or more antioxidants as stabilizer(s).

In this connection, the simultaneous presence of phosphocholines and/or phosphocholine derivatives, in particular alkylphosphocholines, in the compositions according to the invention is excluded.

The present invention relates in particular to the 3-alkoxy-1,2-propanediols. The glycerol monoalkyl ethers according to the invention can be present as racemate (D,L) or in the form of enantiomer-enriched mixtures of the D- or L-form, or in the form of the pure enantiomers.

In one embodiment, the alkyl chain is interrupted by up to 4 oxygen atoms, is therefore introduced by an alcohol group which is accessible from an alcohol or diol by reaction with ethylene oxide and/or propylene oxide. In another embodiment, the alkyl group is a hydrocarbon group.

Here, the alkyl chain in the alkyl group R of the glycerol monoalkyl ether can contain alkyleneoxy groups, such as, for example, ethyleneoxy and/or propyleneoxy groups.

The alkyl group preferably contains 6 to 12 carbon atoms, particularly preferably 6 to 10 carbon atoms, in particular 8 carbon atoms, e.g. a preferred alkyl group is a hydrocarbon group having 8 carbon atoms, in particular a 2-ethylhexyl group. Thus, the particularly preferred glycerol monoalkyl ether is 3-[(2-ethylhexyl)oxy]-1,2-propanediol, which is marketed under the trade name Sensiva® SC 50 by Schulke & Mayr.

Antioxidants which act according to the invention as stabilizers for the glycerol monoalkyl ethers are acetylcysteine, 3-tert-butyl-4-hydroxyanisole, 2,6-di-tert-butyl-p-cresol, tert-butylhydroquinone, caffeic acid, chlorogenic acid, cysteine, cysteine hydrochloride, decylmercaptomethyl-imidazole, diamylhydroquinone, di-tert-butylhydro-quinone, dicetyl thiodipropionate, digalloyl trioleate, dilauryl thiodipropionate, dimyristyl thiodipropionate, dioleyl tocopheryl methylsilanol, disodium rutinyl disulphate, distearyl thiodipropionate, ditridecyl thiodipropionate, dodecyl gallate, erythorbic acid, ethyl ferulate, ferulic acid, hydroquinone, p-hydroxyanisole, hydroxylamine hydrochloride, hydroxylamine sulphate, isooctyl thioglycolate, kojic acid, madecassicoside, methoxy-PEG-7-rutinyl succinate, nordihydroguaiaretic acid, octyl gallate, phenylthioglycolic acid, phloroglucinol, propyl gallate, rosmarinic acid, rutin, sodium erythorbate, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocophersolan, tocopherol (e.g. vitamin E) and its derivatives (e.g. vitamin E derivatives such as vitamin E acetate, vitamin E linoleate, vitamin E nicotinate and vitamin E succinate), o-tolylbiguanide, tris (nonylphenyl) phosphite, dexpanthenol, alpha-hydroxycarboxylic acids (e.g. glycolic acid, lactic acid, mandelic acid) and salts thereof, p-hydroxybenzoic esters (e.g. methyl, ethyl, propyl or butyl esters thereof), dimethyloldimethylhydantoin, N-acylamino acids and salts thereof (e.g. N-octanoylglycine, Lipacide C8G) and hinokitol. Of these, vitamin E and its derivatives, 3-tert-butyl-4-hydroxyanisole and 2,6-di-tert-butyl-p-cresol are preferred, and vitamin E and vitamin E acetate are more preferred.

In this connection, preference is given to antioxidants which already have a physiologically favourable action independently of glycerol monoalkyl ethers, or display said action in—possibly synergistic—combination with the glycerol monoalkyl ether.

The tocopherols are particularly effective antioxidants according to the invention (see the experiments in Table 1 of Example 1). In addition, the tocopherols are particularly desirable antioxidants with regard to the applications, which are associated with strict legal provisions and toxicity tests, of the compositions comprising glycerol monoalkyl ethers according to the invention in the preparation of cosmetics and pharmaceuticals.

Tocopherols occur in plant oils, those being particularly rich in tocopherols being seed oils from soya, wheat, maize, rice, cotton, lucerne and nuts, fruits and vegetables such as raspberries, legumes, fennel, paprika and celery.

The physiological action of tocopherols is based on their properties as free-radical scavengers. Thus, the tocopherols, if they are used according to the invention as antioxidants and thus also pass in small amounts into the preparations provided with glycerol alkyl ethers, can for their part act as physiologically active antioxidants even in the cell membrane and in lipoproteins. Alpha-tocopherol (vitamin E, antisterility factor) is the most physiologically effective and most widespread natural tocopherol.

Although the tocopherols used may be of synthetic origin, tocopherols of natural origin can be used. It is possible to use sterically uniform enantiomers or enantiomer mixtures of tocopherols and accordingly, for the derivatization to acetate, succinate, linoleate or nicotinate, it is possible to use tocopherols of natural and/or synthetic origin and sterically uniform enantiomers or mixtures of tocopherols (in particular alpha-tocopherol).

Here, the compositions according to the invention, i.e. in particular the concentrates and working solutions, are preferably free from ascorbic acid and its derivatives (see Experiments H, N, I and O in Table 1 in Example 1). In a further preferred embodiment of the invention, the presence of sulphite, hydrogensulphite, disulphite and/or disulphide is excluded.

The compositions according to the invention can also comprise additives having an auxiliary and/or additive and/or active ingredient function. Such additives are, for example, water, alcohols, such as ethanol, propanols, benzyl alcohol, phenylalkanols, polyols, such as ethylene glycol, propylene glycol, glycerol, butanediols, pentanediols, silicone compounds, such as cyclomethicones, deodorant active ingredients, such as triclosan, farnesol, triethyl citrate, diglycerol caprate, chitosan, monolaurin, aluminium salts, zirconium salts, fragrances, odour absorbers, surfactants, such as anionic surfactants, nonionic surfactants (e.g. alkyl polyglycosides), amphoteric surfactants, preservatives, antimicrobial active ingredients, dibromodicyanobutane, biocides, fungicides, virucides, antiinflammatories, emollients, moisturizers, refatting active ingredients, skincare substances, skin protection substances, perfumes, dyes, thickeners, buffers. Preferred additives which can be added to the compositions according to the invention are water and/or alcohols and/or polyols, in particular water, ethanol and propylene glycol, and mixtures thereof.

In a preferred embodiment, the antioxidant and its amount (in particular its weight ratio to the glycerol monoalkyl ether) is chosen such that, following storage of the composition at room temperature for one or two years, the Merckoquant® peroxide test registers a peroxide content of less than 5 ppm, more preferably even 0.5 or less ppm, of $H_2O_2$. Examples of such antioxidants and compositions according to the invention are given in Example 1, and compositions based thereon using the other said antioxidants can, if desired, be mixed. Alternatively, the antioxidant and the amount thereof can be chosen such that, following storage of the composition at room temperature for 6 months, the peroxide number is 1 or less than 1, and exemplary compositions are given in Example 2.

In this connection, the composition according to the invention is preferably formulated with additive such that it does not contain a buffer or a buffer mixture, particularly when, as described later, it is in the form of a concentrate.

The compositions according to the invention are characterized by the fact that the glycerol monoalkyl ether is stabilized by comparatively small amounts of antioxidant. In this connection, the weight ratio (wt./wt.) of glycerol monoalkyl ether to antioxidant in the composition according to the invention (concentrate, working solution) is in the range from 50,000:1 to 1:20, preferably 20,000:1 to 1:5, more preferably 10,000:1 to 1:2, e.g. 9995:5 or 1:1.8.

If the composition is in the form of a concentrate, then the concentrate comprises 80 or more % by weight, preferably 90 or more % by weight, more preferably 95 or more % by weight, in particular 99 or more % by weight, of glycerol monoalkyl ether.

Such a concentrate can, for example, comprise from 95 to 99.999% by weight, preferably from 99 to 99.99% by weight, more preferably from 99.5 to 99.95% by weight, e.g. 99.9% by weight or 99.95% by weight, of glycerol monoalkyl ether.

Concentrates according to the invention are preferably additive-free or at least low-additive, i.e. they comprise 30% by weight or less, preferably 10% by weight or less, of additive, in particular anhydrous concentrates are preferred. Particular preference is given to concentrates which consist only of glycerol monoalkyl ether and antioxidant, i.e. do not comprise additive.

In this connection, the weight ratio (wt./wt.) of glycerol monoalkyl ether to antioxidant in the concentrate can be in the range from 20,000:1 to 50:1, preferably 10,000:1 to 100:1, more preferably 5000:1 to 500:1, e.g. 9995:5 or 999:1.

Exemplary concentrates according to the invention, which all comprise the preferred 3-[(2-ethylhexyl)oxy]-1,2-propanediol, consist of 99.5 to 99.95% by weight of this preferred glycerol monoalkyl ether and 0.05 to 0.5% by weight of an antioxidant chosen from the group consisting of vitamin E and its derivatives, 3-tert-butyl-4-hydroxyanisole and 2,6-di-tert-butyl-p-cresol, preferably vitamin E and vitamin E acetate, and mixtures thereof, and consisting in particular only of 3-[(2-ethylhexyl)oxy]-1,2-propanediol and antioxidant, i.e. they comprise none of said additives.

Particularly preferred concentrates according to the invention are a) 99.95% by weight of 3-[(2-ethylhexyl)oxy]-1,2-propanediol and 0.05% by weight of antioxidant chosen from vitamin E and vitamin E derivatives and mixtures thereof, and b) 99.9% by weight of 3-[(2-ethylhexyl)oxy]-1,2-propanediol and 0.1% by weight of antioxidant chosen from vitamin E and vitamin E derivatives and mixtures thereof.

Compositions according to the invention, e.g. concentrates, may, for example, be characterized in that they have a pH of from 2 to 4, preferably 2.5 to 3.5, more preferably 2.8 to 3.2, e.g. 3.

On the other hand, the composition according to the invention can also be in the form of a working solution. Such a working solution comprises 60% by weight or less, preferably 40% by weight or less, more preferably 20% by weight or less, of glycerol monoalkyl ethers. For example, a concentrate according to the invention can be dissolved, i.e. diluted, in a suitable amount of an additive. It is also possible to prepare a working solution according to the invention by adding a corresponding amount of glycerol monoalkyl ether (e.g. 3-[(2-ethylhexyl)oxy]-1,2-propanediol) and antioxidant in any order to one or more of the additives (e.g. water, alcohols and/or polyols). In this connection, the glycerol monoalkyl ether:antioxidant weight ratio can be in the ratio ranges given above for the concentrates according to the invention, e.g. when the working solution is obtained directly from the concentrate by dilution.

Alternatively, if desired, the optimum amount of antioxidant (e.g. the weight ratio of glycerol monoalkyl ether to antioxidant) can, in a specific application case, be determined by the person skilled in the art by means of a few experiments or can arise directly from the desired application. Thus, further possible weight ratios (wt./wt.) of glycerol monoalkyl ether to antioxidant in the working solution are in the range from 20:1 to 1:20, preferably 10:1 to 1:10, more preferably 5:1 to 1:5, e.g. 2:1 or 1:2.

Preferred compositions have a pH of from 2 to 4, preferably 2.5 to 3.5, more preferably 2.8 to 3.2, in particular 3. If the composition, e.g. as concentrate, is anhydrous, then this pH refers for this specific composition according to the invention to a 50% strength mixture of the composition with water, the pH of which is then determined conventionally.

The compositions according to the invention, i.e. in particular the concentrates and working solutions, can be added to cosmetic and/or pharmaceutical preparations, for example, as is correspondingly already known from the use of glycerol monoalkyl ethers from EP 0 599 433 A1 and DE 41 40 474 A1. Furthermore, it is also possible to use the compositions according to the invention in technical products which are to be provided with glycerol monoalkyl ethers and in which peroxides are undesired, e.g. preparations comprising compounds which contain dyes or perfumes or which are unsaturated or sensitive to oxidation. Such preparations or technical products are, for example, deodorant preparations, skincare preparations, sunscreen preparations, baby products, cosmetics for sensitive skin, cosmetic preparations, such as aftershaves, cosmetics based on or partially based on natural raw materials, stabilizers for cosmetic and/or pharmaceutical preparations, disinfectants for skin, hands and wounds, antiseptics, antimicrobial washing lotions, compositions for hair treatment and antimicrobial lubricants. Particular preference is given to the use of the concentrates and working solutions according to the invention in deodorant preparations and skincare preparations.

The addition or incorporation of the compositions according to the invention, i.e. concentrates and working solutions, is usually carried out such that the corresponding cosmetic and/or pharmaceutical preparation is provided with 0.05 to 5% by weight, preferably 0.1 to 1% by weight, more preferably 0.2 to 0.6% by weight, e.g. 0.3% by weight or 0.5% by weight, of glycerol monoalkyl ether.

The compositions, concentrates and working solutions according to the invention, and the cosmetic and/or pharmaceutical preparations can be in the form of solid, semi-solid or liquid, gel-like or emulsion-like preparations.

The compositions are prepared by simple mixing, e.g. the glycerol monoalkyl ether (in particular Sensiva® SC 50) is initially introduced, the antioxidant (e.g. vitamin E or vitamin E derivatives, dissolved or preferably as the pure substance) is dissolved with stirring and, where appropriate, the additives are homogeneously stirred in.

According to the invention, it has surprisingly been found that compositions which comprise a combination of one or more glycerol monoalkyl ethers with an antioxidant or two or more antioxidants as stabilizers are storable and stable for a few months to a few years under practical conditions, i.e. at 0° C. to 40° C. The good handleability of concentrates according to the invention is particularly advantageous.

The invention offers the following advantages:

The formation of peroxides, detectable by measuring the peroxide number or using the Merckoquant® peroxide test analysis strips, can be avoided or at least severely restricted.

The content in stored compositions according to the invention, in particular concentrates, of undesired degradation products of low molecular weight is significantly reduced.

The neck-in effect can be avoided.

The applications-related difficulties for pharmaceutical and/or cosmetic preparations which it has hitherto not been possible to exclude when using glycerol monoalkyl ethers are avoided.

Virtually no changes in odour occur during storage.

The probability of incompatibilities with other cosmetic ingredients is reduced.

The invention described is able to utilize the full potential of glycerol monoalkyl ethers for cosmetic and/or pharmaceutical applications.

The surprising effects which are achieved are illustrated by the examples below.

EXAMPLES

In the examples below, the proportions in the mixtures are given in % by weight.

The following terms are used in the examples below:

| | |
|---|---|
| BHT | 2,6-di-tert-butyl-p-cresol, obtainable from Fluka |
| BHA | 3-tert-butyl-4-hydroxyanisole, obtainable from Fluka |
| Ascorbyl palmitate | 6-0-palmitoyl-L-ascorbic acid, obtainable from Fluka |
| Sensiva ® SC 50 | 3-[(2-ethylhexyl)oxy]-1,2-propanediol |
| Lipacide C8G | N-octanoylglycine, obtainable from Seppic | n.c. = no change,
d. = days,
m. = months,
w. = weeks,
y. = years,
n.d. = not detectable,
cl = clear,
c = colourless,
kr = crystals,
yl = yellowish,
S. = start of the investigation.

The data in "ppm of $H_2O_2$" refer to the peroxide determination using Merckoquant® peroxide test analysis strips. This semiquantitative method for determining peroxide was carried out as follows:

About 0.5 g of the sample to be investigated is placed in a test tube and treated with the same amount of demineralized water. The two phases are mixed by shaking, and a Merckoquant® peroxide test analysis strip is dipped in for one second. The damp strip is removed from the liquid and the peroxide content is read off after 15 seconds using the reference scale and noted. If the peroxide content is too high, the amount is doubled with demineralized water, again shaken etc., until a reading is possible using the reference scale. The value obtained is back-calculated using the dilution.

The peroxide number (PON) gives the amount of peroxide in milliequivalents of active oxygen which is present in 1000 g of substance, determined in accordance with the method below.

5.00 g of substance are weighed into a 250 ml Erlenmeyer flask with ground-glass stopper and dissolved in 30 ml of a mixture of 2 parts by volume of chloroform R and 3 parts by volume of acetic acid 98% R with shaking. Following the addition of 0.5 ml of saturated potassium iodide solution R, the solution is shaken for exactly 1 minute, then treated with 30 ml of water and slowly titrated with 0.01 N sodium thiosulphate solution with continuous shaking until the yellow coloration has virtually disappeared. Following the addition of 5 ml of starch solution R, the titration is continued with vigorous shaking until the blue coloration disappears ($n_1$ ml of 0.01 N sodium thiosulphate solution). A control experiment is carried out under the same conditions ($n_2$ ml of 0.01 N sodium thiosulphate solution). For this, at most 0.1 ml of 0.01 N sodium thiosulphate solution must be consumed.

The peroxide number is calculated as follows:

$$PON = \frac{10(n_1 - n_2)}{m}$$

where m is the initial weight of the substance in grams.

The method is explained in more detail in DAB 9-Kommentar [German Pharmacopoeia 9—Commentary] (K. Hartke, E. Mutschler, Editor, Wissenschaftliche Verlagsgesellschaft mbH Stuttgart, 9th edition 1986).

Example 1

3-[(2-ethylhexyl)oxy]-1,2-propanediol was mixed with a variety of substances, and the stability of the compositions during storage at room temperature in blue polyethylene bottles was tested (sample A (Alu) was stored in an aluminium container). Following preparation of the samples, the value for ppm of $H_2O_2$ and the pH were determined at regular intervals.

The pH of the anhydrous solutions is given as the value which a 50% strength slurry of the respective anhydrous solution in demineralized water has, determined using Merck® pH indicator strips.

The results of the individual experiments are given in Table 1. In this connection, information such as, for example, "2–5" for the ppm of $H_2O_2$ value means that the value on the reference scale is between two values, for example between 2 and 5.

TABLE 1

| | | A(Alu) | A | B | C | D | E | F | G |
|---|---|---|---|---|---|---|---|---|---|
| BHT | | | | 0.10 | 0.05 | 0.10 | | | |
| BHA | | | | | | | 0.05 | | |
| Vitamin E, Fluka | | | | | | | | 0.10 | 0.05 |
| Sensiva ® SC 50 | | 100.00 | 100.00 | 99.90 | 99.95 | 99.90 | 99.95 | 99.90 | 99.95 |
| PON S. | | 0.5 | 0.5 | 0.5 | 0.5 | 0.5 | 0.5 | 0.5 | 0.5 |
| ppm of $H_2O_2$ | 7 d. | 0.5 | 2 | 0.5 | 0.5 | 0.5 | 0.5 | 0.5 | 0.5 |
| pH | 7 d. | 3 | 3 | 3 | 3 | 3 | 3 | 3 | 3 |
| ppm of $H_2O_2$ | 9 d. | 0.5–1 | 2 | 0.5 | 0.5 | 0.5 | 0.5 | 0.5 | 0.5 |
| pH | 9 d. | 3 | 3 | 3 | 3 | 3 | 3 | 3 | 3 |
| ppm of $H_2O_2$ | 2 w. | 2 | 2–5 | 0.5 | 0.5 | 0.5 | 0.5 | 0.5 | 0.5 |
| pH | 2 w. | 3 | 3 | 3 | 3 | 3 | 3 | 3 | 3 |
| ppm of $H_2O_2$ | 3 w. | 2–5 | 2–5 | 0.5 | 0.5 | 0.5 | 0.5 | 0.5 | 0.5 |
| pH | 3 w. | 3 | 3 | 3 | 3 | 3 | 3 | 3 | 3 |
| ppm of $H_2O_2$ | 4 w. | 2–5 | 2–5 | 0.5 | 0.5 | 0.5 | 0.5 | 0.5 | 0.5 |
| pH | 4 w. | 3 | 3 | 3 | 3 | 3 | 3 | 3 | 3 |
| ppm of $H_2O_2$ | 5 w. | 2–5 | 2–5 | 0.5 | 0.5 | 0.5 | 0.5 | 0.5 | 0.5 |
| pH | 5 w. | 3 | 3 | 3 | 3 | 3 | 3 | 3 | 3 |
| ppm of $H_2O_2$ | 6 w. | 2–5 | 2–5 | 0.5 | 0.5 | 0.5 | 0.5 | 0.5 | 0.5 |
| pH | 6 w. | 3 | 3 | 3 | 3 | 3 | 3 | 3 | 3 |
| ppm of $H_2O_2$ | 7 w. | 5 | 2–5 | 0.5 | 0.5 | 0.5 | 0.5 | 0.5 | 0.5 |
| pH | 7 w. | 3 | 3 | 3 | 3 | 3 | 3 | 3 | 3 |
| ppm of $H_2O_2$ | 8 w. | 5 | 2–5 | 0.5 | 0.5 | 0.5 | 0.5 | 0.5 | 0.5 |
| pH | 8 w. | 3 | 3 | 3 | 3 | 3 | 3 | 3 | 3 |
| Hazen colour number | 8 w. | | <5 | <5 | | <5 | | <5 | |
| ppm of $H_2O_2$ | 2 m. | 25 | 2–5 | 0.5 | 0.5 | 0.5 | 0.5 | 0.5 | 0.5 |
| pH | 2 m. | 3 | 3 | 3 | 3 | 3 | 3 | 3 | 3 |
| ppm of $H_2O_2$ | 3 m. | 25–50 | 2–5 | 0.5 | 0.5 | 0.5 | 0.5 | 0.5 | 0.5 |
| ppm of $H_2O_2$ | 4 m. | 25–50 | 5 | 0.5 | 0.5 | 0.5 | 0.5 | 0.5 | 0.5 |
| ppm of $H_2O_2$ | 5 m. | 50 | 5 | 0.5 | 0.5 | 0.5 | 0.5 | 0.5 | 0.5 |
| ppm of $H_2O_2$ | 6.5 m. | 50 | 5 | 0.5 | 0.5 | 0.5 | 0.5 | 0.5 | 0.5 |
| ppm of $H_2O_2$ | 8.5 m. | 25–50 | 5 | 0.5 | 0.5 | 0.5 | 0.5 | 0.5 | 0.5 |
| ppm of $H_2O_2$ | 11 m | 10–25 | 10 | 0.5 | 0.5 | 0.5 | 0.5 | 0.5 | 0.5 |
| ppm of $H_2O_2$ | 1 y. | 10 | 10 | 0.5 | 0.5 | 0.5 | 0.5 | 0.5 | 0.5 |
| ppm of $H_2O_2$ | 14 m. | 10 | 10 | 0.5 | 0.5 | 0.5 | 0.5 | 0.5 | 0.5 |
| ppm of $H_2O_2$ | 16 m. | 10 | 10 | 0 | 0 | 0 | 0 | 0 | 0 |
| ppm of $H_2O_2$ | 2 y. | 0 | 10–25 | 0 | 0.5 | 0 | 0 | 0 | 0 |
| Appearance of the bottle | 2 y. | n.c. | neck in | n.c. | n.c. | n.c. | nc. | n.c. | nc. |
| PON | 2 y. 11 m. | | 25.3 | 0.2 | | 0.4 | | n.d. | n.d. |
| Appearance of the bottle | 2 y. 11 m. | n.c. | considerable neck in | n.c. | nc. | n.c. | n.c. | n.c. | n.c. |

| | | H | I | J | K | L | M | N | O |
|---|---|---|---|---|---|---|---|---|---|
| BHT | | | | | | 0.05 | 0.025 | | |
| BHA | | | | | | 0.05 | 0.025 | | |
| Vitamin E, Fluka | | | | | | | | 0.05 | 0.025 |
| Ascorbyl palmitate | | 0.10 | 0.05 | | | | | 0.05 | 0.025 |
| Dexpanthenol | | | | 0.10 | 0.05 | | | | |
| Sensiva ® SC 50 | | 99.90 | 99.95 | 99.90 | 99.95 | 99.90 | 99.95 | 99.90 | 99.95 |
| PON S. | | 0.5 | 0.5 | 0.5 | 0.5 | 0.5 | 0.5 | 0.5 | 0.5 |
| ppm of $H_2O_2$ | 7 d. | 0.5 | 0.5 | 0.5–2 | 0.5–2 | 0.5 | 0.5 | 0.5 | 0.5 |
| pH | 7 d. | 3 | 3 | 3 | 3 | 3 | 3 | 3 | 3 |
| ppm of $H_2O_2$ | 9 d. | 0.5 | 0.5 | 2 | 2 | 0.5 | 0.5 | 0.5 | 0.5 |
| pH | 9 d. | 3 | 3 | 3 | 3 | 3 | 3 | 3 | 3 |
| ppm of $H_2O_2$ | 2 w. | 0.5–2 | 0.5–2 | 2 | 3 | 0.5 | 0.5 | 0.5 | 0.5 |
| pH | 2 w. | 3 | 3 | 3 | 3 | 3 | 3 | 3 | 3 |
| ppm of $H_2O_2$ | 3 w. | 2–5 | 2 | 2–5 | 2–5 | 0.5 | 0.5 | 0.5–2 | 0.5–2 |
| pH | 3 w | 3 | 3 | 3 | 3 | 3 | 3 | 3 | 3 |
| ppm of $H_2O_2$ | 4 w. | 2–5 | 2–5 | 2–5 | 2–5 | 0.5 | 0.5 | 0.5–2 | 0.5–2 |
| pH | 4 w. | 3 | 3 | 3 | 3 | 3 | 3 | 3 | 3 |
| ppm of $H_2O_2$ | 5 w. | 2–5 | 2–5 | 2–5 | 2–5 | 0.5 | 0.5 | 2 | 2 |
| pH | 5 w. | 3 | 3 | 3 | 3 | 3 | 3 | 3 | 3 |
| ppm of $H_2O_2$ | 6 w. | 10 | 5 | 2–5 | 2–5 | 0.5 | 0.5 | 2 | 2 |
| pH | 6 w. | 3 | 3 | 3 | 3 | 3 | 3 | 3 | 3 |
| ppm of $H_2O_2$ | 7 w. | 10 | 5 | 2–5 | 2–5 | 0.5 | 0.5 | 2–5 | 2 |
| pH | 7 w | 3 | 3 | 3 | 3 | 3 | 3 | 3 | 3 |
| ppm of $H_2O_2$ | 8 w. | 25 | 10 | 2–5 | 2–5 | 0.5 | 0.5 | 2–5 | 2 |
| pH | 8 w. | 3 | 3 | 3 | 3 | 3 | 3 | 3 | 3 |
| Hazen colour number | 8 w. | <5 | | <5 | | <5 | | <5 | |
| ppm of $H_2O_2$ | 2 m. | 25 | 10–25 | 2–5 | 2–5 | 0.5 | 0.5 | 2–5 | 2 |
| pH | 2 m. | 3 | 3 | 3 | 3 | 3 | 3 | 3 | 3 |
| ppm of $H_2O_2$ | 3 m. | 25–50 | 25 | 2–5 | 2–5 | 0.5 | 0.5 | 5 | 5 |
| ppm of $H_2O_2$ | 4 m. | 50 | 25–50 | 2–5 | 2–5 | 0.5 | 0.5 | 5 | 5 |
| ppm of $H_2O_2$ | 5 m. | 50–100 | 50 | 5 | 5 | 0.5 | 0.5 | 5–10 | 5 |
| ppm of $H_2O_2$ | 6.5 m. | 100 | 50 | 5 | 5 | 0.5 | 0.5 | 10 | 5 |
| ppm of $H_2O_2$ | 8.5 m. | 100–200 | 100 | 5 | 5 | 0.5 | 0.5 | 10 | 5 |

TABLE 1-continued

| | | | | | | | | | |
|---|---|---|---|---|---|---|---|---|---|
| ppm of $H_2O_2$ | 11 m. | 200 | 100 | 5 | 5 | 0.5 | 0.5 | 10 | 5 |
| ppm of $H_2O_2$ | 1 y. | 200 | 100 | 5 | 5 | 0.5 | 0.5 | 10 | 5 |
| ppm of $H_2O_2$ | 14 m. | 100 | 160 | 5 | 5 | 0.5 | 0.5 | 5 | 2 |
| ppm of $H_2O_2$ | 16 m. | 100 | 100 | 5 | 5–10 | 0 | 0 | 5 | 5 |
| ppm of $H_2O_2$ | 2 y. | 10–25 | 25 | 5 | 5 | 0 | 0 | 2–5 | 2–5 |
| Appearance of the bottle | 2 y. | neck in | neck in | n.c. | n.c. | n.c. | nc. | n.c. | nc. |
| PON | 2 y. 11 m. | 19.5 | | | | | | | |
| Appearance of the bottle | 2 y. 11 m. | considerable neck in | considerable neck in | n.c. | nc. | n.c. | n.c. | n.c. | nc. |

The experiments listed in Table 1 thus demonstrate that BHT, BHA, vitamin E and dexpanthenol stabilize the glycerol monoalkyl ethers over a long period, and in particular that the appearance of peroxides, determined by the Merckoquant® peroxide test, is avoided and as a result the neck-in effect is no longer observed when said antioxidants are used. The pH of the samples, as shown by reference to the measurement after 2 months, remains unchanged.

It is notable that according to the invention even 0.05% by weight of the antioxidants BHT, BHA, vitamin E and dexpanthenol, which are used by way of example, exhibit the stabilizing effect.

By contrast, ascorbyl palmitate does not stabilize the glycerol monoalkyl ethers (see Experiments H and I) or inhibit its stabilization by vitamin E (see Experiments N and O), the lack of stabilizing effect, or destabilization, being significantly marked after storage for just 8 weeks. Accordingly, the compositions according to the invention (concentrates, working solutions) are preferably free from ascorbic acid or ascorbic acid derivatives and salts.

Example 2

The peroxide number of compositions of Sensiva® SC 50 and Lipacide C8G salts was compared with the stability of mixtures of Sensiva® SC 50 and other salts. The results of individual experiments with a sample of Sensiva® SC 50, which already has a low content of peroxide, are given in Table 2.

In the presence of Lipacide C8G sodium salts, the peroxide number decreases as a function of time, and at the same time the neck-in effect is avoided. This effect could not be achieved using sodium sulphate and sodium citrate solutions.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A concentrate comprising
    a) from about 99.5 to about 99.95% by weight of 3-[(2-ethylhexyl)oxy]-1,2-propanediol; and
    b) about 0.05 to about 0.5% by weight of an antioxidant selected from the group consisting of vitamin E and its derivatives, 3-tert-butyl-4-hydroxyanisole and 2,6-di-tert-butyl-p-cresol, and mixtures thereof.

2. The concentrate according to claim 1, comprising about 99.9% by weight of 3-[(2-ethylhexyl)oxy]-1,2-propanediol and about 0.1% by weight of antioxident selected from the group consisting of vitamin E, vitamin E derivatives, and mixtures thereof.

3. The concentrate according to claim 1, comprising about 99.95% by weight of 3-[(2-ethylhexyl)oxy]-1,2-propanediol and about 0.05% by weight of antioxidant selected from the

TABLE 2

| | | A | B | C | D | E |
|---|---|---|---|---|---|---|
| 20% strength aqueous solution of Lipacide C8G as Na salt | | | 90 | 3 | | |
| 15% strength aqueous solution of Na citrate | | | | | 3 | |
| 15% strength aqueous Na sulphate solution | | | | | | 3 |
| Sensiva ® SC 50 | | 100 | 10 | 97 | 97 | 97 |
| Appearance S. | | | cl c | cl c | cl c | not dissolved, filtered |
| PON S. | | | 10 | 10 | 10 | 10 |
| PON | 4 d. | 10 | 0.5 | 10 | 10 | 10 |
| PON | 9 d. | 10–25 | 0 | 10 | 25 | 25 |
| PON | 6 w. | 25 | 0 | 10 | 25 | 25 |
| PON | 11 w. | 25 | 0 | 10 | 25 | 25 |
| PON | 6 m. | 20 | 0 | 1 | 5 | 10 |
| PON | 2 y. 2 m. | 5–10 | 0 | 0 | 2–5 | 2–5 |
| PE bottle | 2 y. 2 m. | considerable neck in | n.c. | nc. | neck in | neck in |
| Appearance | | cl c | cl yl | cl yl | kr c | cl c |
| Hazen colour number | | 0 | 62 | 43 | 2 | 0 |

Result:

group consisting vitamin E, vitamin E derivatives, and mixtures thereof.

4. The concentrate according to claim 1, wherein the concentrate has a pH of 2 to 4.

5. The concentrate according to claim 4, wherein the concentrate has a pH of 2.5 to 3.5.

6. The concentrate according to claim 5, wherein the concentrate has a pH of 2.8 to 3.2.

7. The concentrate according to claim 6, wherein the concentrate has a pH of 3.

8. The concentrate according to claim 1, wherein the concentrate has a pH of 2 to 4.

9. The concentrate according to claim 1, wherein the antioxidant is selected from the group consisting of vitamin E and vitamin E acetate.

10. The concentrate according to claim 1, wherein the concentrate has a pH of between 2.5 and 3.5.

11. The concentrate according to claim 1, wherein the concentrate has a pH of between 2.8 and 3.2.

12. The concentrate according to claim 1, wherein the concentrate has a pH of 3.

* * * * *